United States Patent [19]
Kato

[11] Patent Number: 6,030,081
[45] Date of Patent: Feb. 29, 2000

[54] EYE REFRACTIVE POWER MEASUREMENT APPARATUS

[75] Inventor: Koki Kato, Gamagori, Japan

[73] Assignee: Nidek Co., Ltd., Japan

[21] Appl. No.: 09/141,347

[22] Filed: Aug. 27, 1998

[30] Foreign Application Priority Data

Aug. 29, 1997 [JP] Japan .................................. 9-249401

[51] Int. Cl.⁷ .................................................. A61B 3/10
[52] U.S. Cl. .......................................................... 351/212
[58] Field of Search .................................. 351/205, 211, 351/212, 214, 221; 356/124, 125, 126

[56] References Cited

U.S. PATENT DOCUMENTS

| | | | |
|---|---|---|---|
| 4,390,255 | 6/1983 | Nohda et al. | 351/212 |
| 4,526,451 | 7/1985 | Nohda | 351/211 |
| 4,702,596 | 10/1987 | Nohda | 351/126 |
| 4,787,743 | 11/1988 | Nohda | 356/124 |
| 4,917,458 | 4/1990 | Matsumura | 354/212 |
| 5,214,456 | 5/1993 | Gersten | 351/212 |
| 5,555,039 | 9/1996 | Iki et al. | 351/205 |

FOREIGN PATENT DOCUMENTS

| | | |
|---|---|---|
| 0 210 722 | 2/1987 | European Pat. Off. . |
| 0 836 830 | 4/1998 | European Pat. Off. . |
| 2951897 | 7/1980 | Germany . |
| 57-165735 | 10/1982 | Japan . |
| 61-11090 | 4/1986 | Japan . |
| 61-48939 | 10/1986 | Japan . |
| 63-46130 | 2/1988 | Japan . |
| 2-53738 | 11/1990 | Japan . |
| 10-108836 | 4/1998 | Japan . |
| 10-108837 | 4/1998 | Japan . |

OTHER PUBLICATIONS

European Search Report dated Jan. 29, 1998 (2 pages).

*Primary Examiner*—George Manuel
*Attorney, Agent, or Firm*—Finnegan, Henderson, Farabow, Garrett & Dunner, L.L.P.

[57] ABSTRACT

An eye refractive power measurement apparatus for measuring a refractive power of an eye to be examined, the apparatus comprising a projecting optical system for scanning and projecting a slit light bundle onto a fundus of the eye to be examined, a photo-receiving optical system provided with a photo-detector arranged at a conjugate position with a cornea of the eye so as to have a predetermined position with respect to a scanning direction of the slit light bundle and an open diaphragm, can be arranged at different predetermined positions, for reducing the slit light bundle, a selecting device for selecting the position of the open diaphragm so as to change a range in which the photo-receiving optical system can detect an eye refractive power and an eye refractive power calculating device to calculate a refractive power of the eye based on an output signal from the photo-detector receiving the slit light bundle reflected from the fundus of the eye through the open diaphragm and the position of the open diaphragm.

19 Claims, 8 Drawing Sheets

EYE REFRACTIVE POWER MEASUREMENT APPARATUS

BACKGROUND OF THE INVENTION

1. Field of the Invention

The present invention relates to an eye refractive power measurement apparatus, and more particularly to the eye refractive power measurement apparatus which measures a refractive power of an eye to be examined.

2. Description of Related Art

One conventionally known eye refractive power measurement apparatus is that an apparatus provided with a projecting optical system which scans and projects a slit light bundle onto a fundus of an eye to be examined and also with a photo-detecting optical system. The photo-detecting optical system includes at least one pair of photo-detectors which is disposed at a conjugate position with a cornea (or an iris) of the eye to be examined and an open diaphragm which is disposed at a conjugate position with a fundus of an emmetropic eye. The apparatus obtains a refractive power of the eye based on output signals from the photo-detectors indicating the phase difference upon receiving the slit light bundle reflected from the fundus of the eye through the open diaphragm.

With this kind of apparatus, by shifting photo-detectors to higher positions with respect to an optical axis, an eye refractive power at a corneal part corresponding to a different height can be obtained. To take advantage of this characteristic, it has been suggested an apparatus which enables to obtain eye refractive powers at plural heights of corneal parts.

However, the following is to be noted here. In case that an eye to be examined is not emmetropic, as the photo-detectors shifted to higher positions (the radius of a corneal part to be measured in a meridian direction becomes larger), the phase difference to be detected becomes bigger. This results in a consequent shift of a measurement point on the fundus toward its periphery. If an absolute value of the refractive power of the eye to be examined is relatively high, the slit light bundle may not be projected within a range of the fundus. This presents the problem that the measurable range narrows as the photo-detectors are shifted to higher positions.

SUMMARY OF THE INVENTION

The present invention has been made in view of the above circumstances and has an object to overcome the above problems and to provide an eye refractive power measurement apparatus which enables to extend a measurable range upon an eye refractive power measurement regardless of height of a corneal part to be measured.

Additional objects and advantages of the invention will be set forth in part in the description which follows and in part will be obvious from the description, or may be learned by practice of the invention. The objects and advantages of the invention may be realized and attained by means of the instrumentalities and combinations particularly pointed out in the appended claims.

To achieve the objects and in accordance with the purpose of the present invention, as embodied and broadly described herein, an eye refractive power measurement apparatus of this invention comprises a projecting optical system for scanning and projecting a slit light bundle onto a fundus of the eye to be examined, a photo-receiving optical system provided with a photo-detector arranged at a conjugate position with a cornea of the eye so as to have a predetermined position with respect to a scanning direction of the slit light bundle and an open diaphragm, can be arranged at different predetermined positions, for reducing the slit light bundle, selecting means for selecting the position of the open diaphragm so as to change a range in which the photo-receiving optical system can detect an eye refractive power and eye refractive power calculating means to calculate a refractive power of the eye based on an output signal from the photo-detector receiving the slit light bundle reflected from the fundus of the eye through the open diaphragm and the position of the open diaphragm.

In another aspect of the present invention, an eye refractive power measurement apparatus comprises a projecting optical system for scanning and projecting a slit light bundle onto a fundus of an eye to be examined, a photo-receiving optical system to detect the slit light bundle reflected from the fundus of the eye by at least one pair of photo-detectors arranged in one meridian direction in symmetric relation with respect to an optical axis so as to be at an approximately conjugate position with a cornea of the eye, eye refractive power calculating means to calculate a refractive power of the eye based on output signals indicating the phase difference among each of the photo-detectors provided in the photo-receiving optical system, the apparatus further comprising an open diaphragm, can be arranged at different predetermined positions, for reducing the slit light bundle and selecting means for selecting the position of the open diaphragm so as to change a range in which the photo-receiving optical system can detect an eye refractive power.

As described above, and in accordance with the present invention, a measurable range upon an eye refractive power measurement can be extended by using an appropriate diaphragm at a different position.

BRIEF DESCRIPTION OF THE DRAWINGS

The accompanying drawings, which are incorporated in and constitute a part of this specification, illustrate embodiments of the present invention and, together with the description, serve to explain the objects, advantages and principles of the invention. In the drawings.

DETAILED DESCRIPTION OF THE PREFERRED EMBODIMENTS

Figure 1:
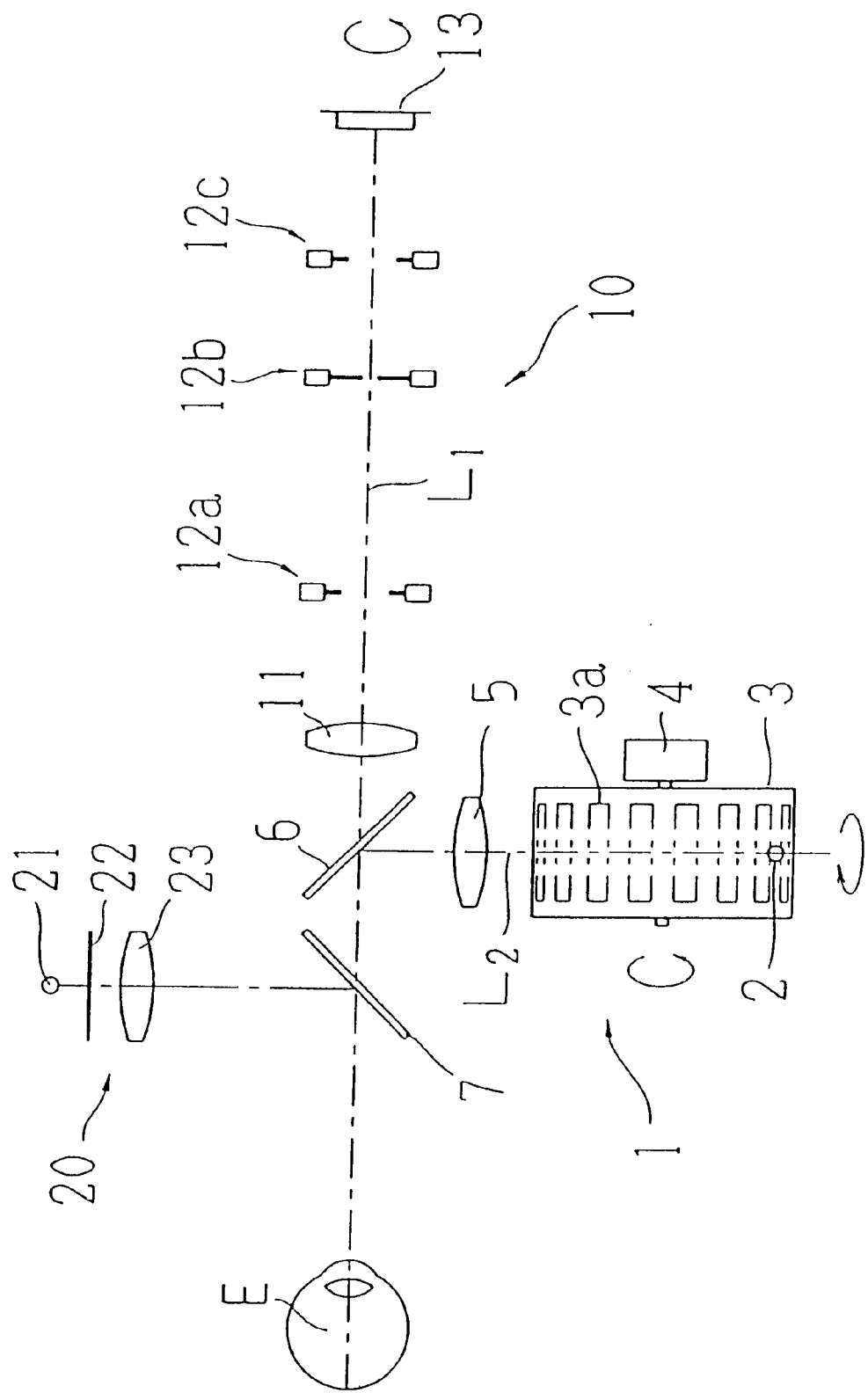
FIG. 1 is a view showing a schematic optical system configuration of an eye refractive power measurement apparatus according to the preferred embodiment of the present invention.

A detailed description of one preferred embodiment of an eye refractive power measurement apparatus embodying the present invention will now be given referring to the accompanying drawings. FIG. 1 is a view showing a schematic optical system configuration of the eye refractive power measurement apparatus. A measurement optical system and a fixation target optical system will be explained separately. The apparatus of this preferred embodiment also includes an alignment optical system and an observation optical system therein. However, these optical systems are not relevant to the present invention and, therefore, the explanations regarding the optical systems are omitted from the specification.

<Measurement optical system>

The measurement optical system is provided with a projecting optical system 1 and a photo-receiving optical system 10. The projecting optical system 1 has a configuration as follows. Reference numeral 2 denotes a slit illumination light source which emits light within a range of near infrared rays, and 3 is a cylindricalshaped rotation sector which is made to be rotated by a motor 4 in the fixed direction with the fixed velocity. The rotation sector 3 is provided with numbers of slit apertures 3a on the side thereof. Element 5 is a projecting lens and the slit illumination light source 2 is arranged in conjugation with a vicinity of a cornea of an eye E to be examined with respect to the projecting lens 5. Element 6 is a beam splitter. The infrared light emitted from the slit illumination light source 2 illuminates the slit apertures 3a provided on the rotation sector 3. The slit light bundle scanned by rotation of the rotation sector 3 passes through the projecting lens 5 and then reflected by the beam splitter 6. Thereafter, the slit light bundle transmits another beam splitter 7 which makes an optical axis of the fixation target optical system coaxial. Having been converged in the vicinity of the cornea of the eye E, the slit light bundle is projected onto a fundus of the eye E.

Figure 2:
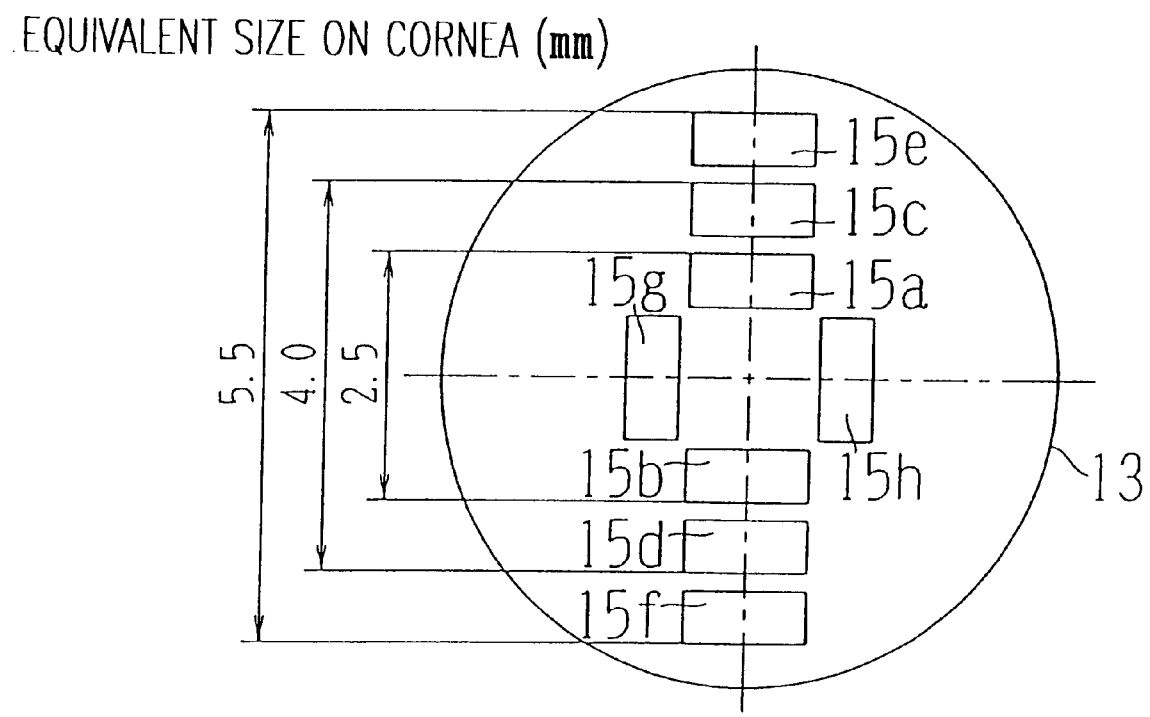
FIG. 2 is a view showing an arrangement of photo-detectors included in a photo-receiving part of the apparatus shown in FIG. 1.

Along the optical path of the photo-receiving optical system 10, a photo-receiving lens 11, three diaphragms 12a, 12b and 12c and a photo-receiving part 13 are provided. The diaphragms 12a, 12b and 12c are variable in diameter and upon a measurement, one of the diaphragms is selected and adjusted to the predetermined diameter. These three diaphragms 12a, 12b and 12c are at conjugate positions respectively with a fundus of a myopic eye having a −5 [Diopter] focal accommodation, a fundus of an emmetropic eye having a 0 [D] focal accommodation and a fundus of a hypermetropic eye having +5 [D] focal accommodation relative to the photo-receiving lens 11. As shown in FIG. 2, the photo-receiving part 13 has eight photo-detectors 15a–15h on the photo-receiving surface thereof. The photo-detectors 15a–15h are approximately at conjugate positions with the cornea (or with an iris) of the eye E with respect to the photo-receiving lens 11. Among these eight photo-detectors, the photo-detectors 15a–15f are disposed along a meridian which crosses an optical axis L1, and the photo-detectors 15a with 15b, 15c with 15d and 15e with 15f are symmetrical in relation to the optical axis L1. The configuration distance of these three pair of the photo-detectors is decided in order to detect an eye refractive power at a corneal part corresponding to a different height in the meridian direction (in FIG. 2, it is shown by the equivalent size on the cornea). On the other hand, the photo-detectors 15g and 15h are arranged along a meridian which crosses the photo-detectors 15a–15f at right angle in symmetric relation with respect to the optical axis L1.

Further, the measurement optical system having above-described configuration is designed so that the slit illumination light source 2, the rotation sector 3 and the motor 4 included in the projecting optical system 1 rotate about an optical axis L2 and the photo-receiving part 13 rotate about the optical axis L1 in synchronism. In addition, the direction in which the photo-detectors 15a–15f arranged on the surface of the photo-receiving part 13 is set so that it crosses the slit light bundle to be projected onto the eye E at its lengthwise direction at the right angle.

<Fixation target optical system>

Reference numeral 20 denotes the fixation target optical system, 21 is a visible light source, 22 is a fixation target and 23 is a projecting lens. The projecting lens 23 fogs the eye E by moving toward the optical axis L1. The visible light source 21 illuminates the fixation target 22 thereafter the light bundle from the fixation target 22 passes through the projecting lens 23 and reaches the beam splitter 7 to be reflected therefrom to the eye E. As a result, the eye E is made to fixedly focus on the fixation target 22.

Next, the method of the eye refractive power measurement will be described. First, the relationship between the positions of the diaphragms (12a, 12b and 12c) and a measurable range determined by the photo-detectors (15a–15f) each of which is arranged at a different height from the optical axis L1 will be described with reference to the FIGS. 3–6.

Figure 3:
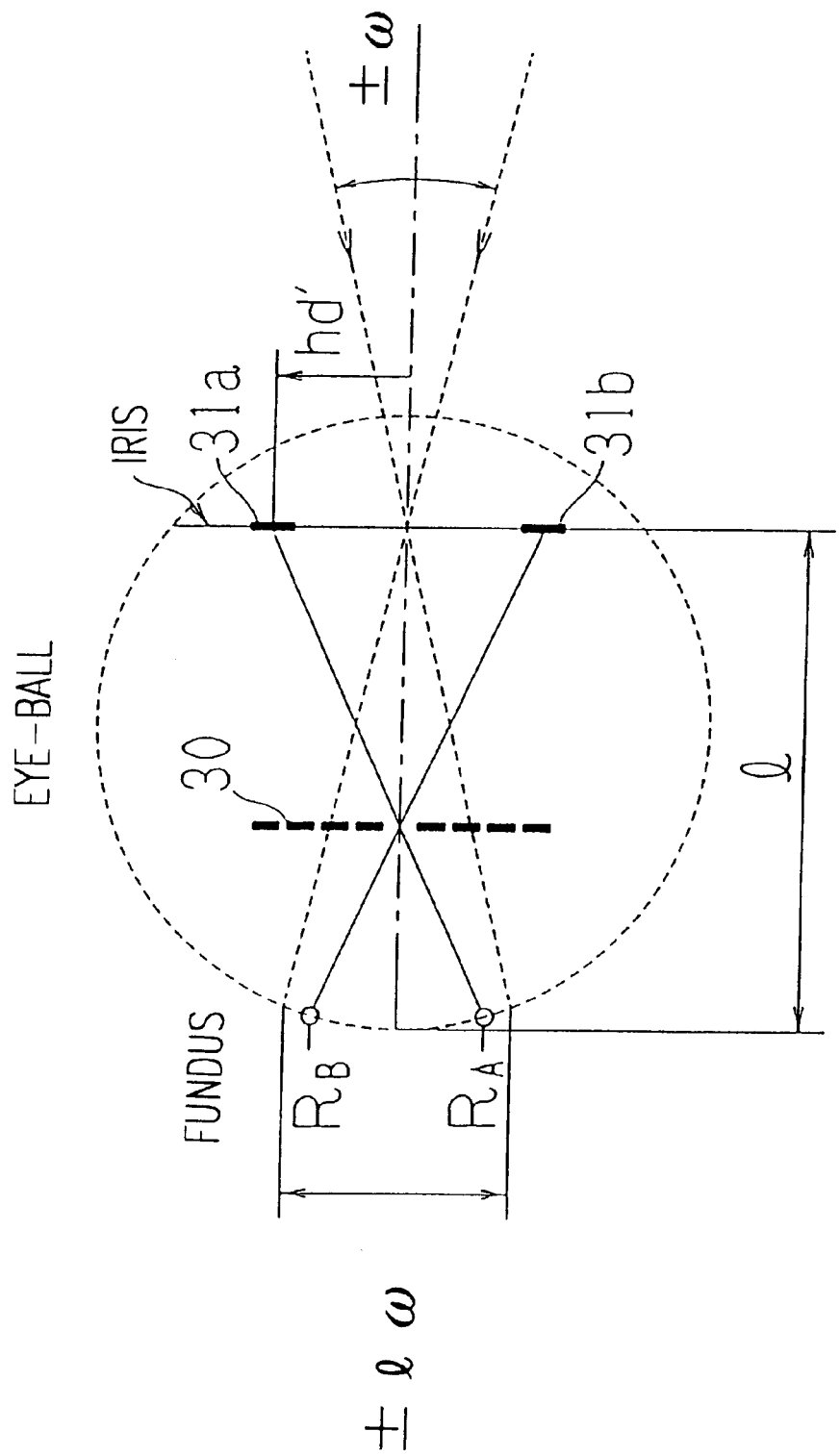
FIG. 3 is a diagram showing the eye E to be examined at the time a diaphragm and photo-detectors arranged in the photo-receiving optical system are projected.

FIG. 3 is a diagram showing the eye E to be examined at the time the diaphragm and the photo-detectors arranged in the photo-receiving optical system 10 are projected. In the figure, reference numeral 30 denotes an image of the diaphragm 12b which is arranged at an approximately conjugate position with respect to an emmetropic eye having a 0 [D] focal accommodation. That is to say, if the eye E is emmetropic, the image 30 of the diaphragm 12b and the fundus of the eye E coincide. In other words, the position of the image 30 of the diaphragm 12b varies depending on the refractive power of the eye E. Reference numerals 31a and 31b are regarded as the images of one of the pairs of the photo-detectors 15a–15f and hd' is regarded as the height from the optical axis L1, at which each image is projected onto the iris.

Let l denote the distance from the iris to the fundus of the eye E, and let it be assumed that the slit light bundle is scanned at an opening angle of ±ω and irradiated onto the fundus, then a range which the slit light bundle scans is expressed as ±lω. When the slit light bundle reaches a point RA, waveform indicating the amount of the light received by the photo-detector corresponding to the image 31a shows its peak. When the slight light bundle reaches a point RB, waveform indicating the amount of the light received by the photo-detector corresponding to the image 31b shows its peak. That is to say the range between the points RA–RB at which the slit light bundle is scanned corresponds to the phase difference. From this, it can be known that as the refractive power of the eye E deviates from 0 [D], the points on the fundus, from which the light bundle reflected into the images 31a and 31b, will shift outward (the distance between the points RA and RB becomes wider). This tendency is more obvious as hd' shifts higher. As is clear from this, the phase difference proportionally relates to the height of the images 31a and 31b (hd') and also to the refractive power of the eye E.

Figure 4:
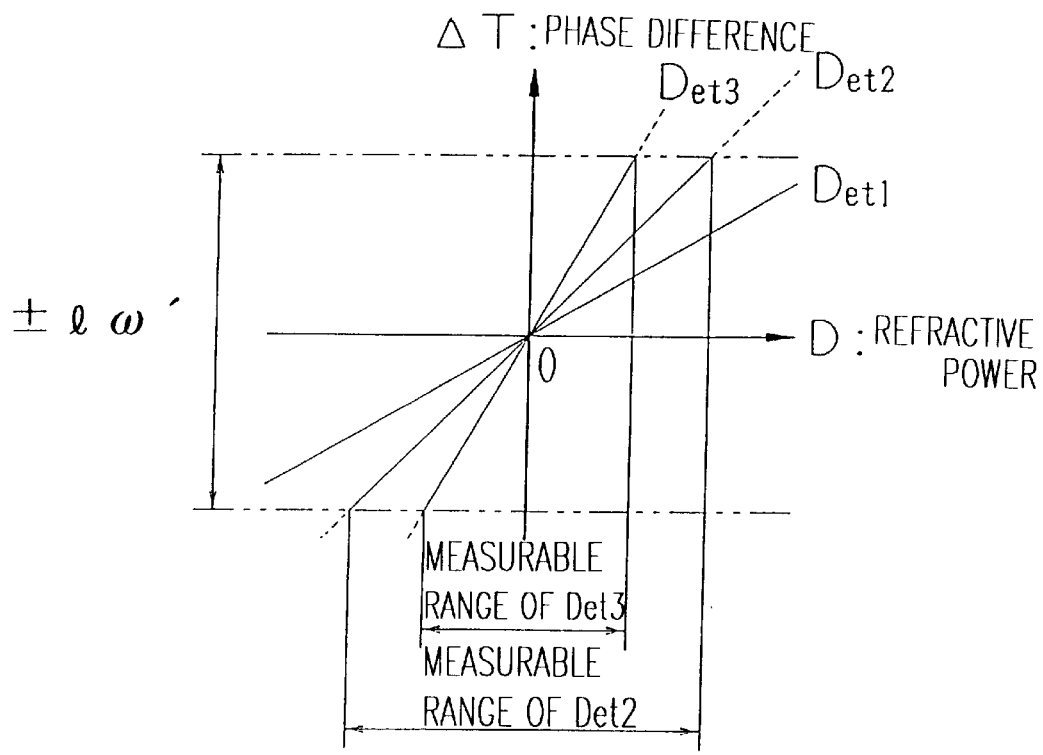
FIG. 4 is a view showing the relationship between the phase difference detected by each pair of the photo-detectors and a refractive power of the eye to be examined in the case of utilizing a diaphragm 12b which is arranged at a conjugate position with respect to a fundus of an emmetropic eye having a 0 [D] focal accommodation.

As above noted, in the case of this embodiment where three pairs of the photo-detectors 15a–15f are disposed at different heights, the relationship between the phase difference detected by each pair of the photo-detectors (15a–15f) and the eye refractive powers is as shown in FIG. 4 (it is assumed that the diaphragm is arranged at a conjugate position with respect to the emmetropic eye E). In FIG. 4, the graph Det1, Det2 and Det3 respectively indicate the relationship with each pair of the photo-detectors 15a and 15b which is the innermost pair, 15c and 15d and lastly 15e and 15f which is the outermost pair.

Here, seeing from the relationship regarding the range of ±l ω on the fundus which can be scanned by the projecting optical system 1, it is noted that the range in which each photo-detector can detect the phase difference is within the range of ±lω' which corresponds to the range of ±lω. Consequently, the measurable ranges by each pair of the photo-detectors shown in the graphs Det1, Det2 and Det3 are limited. Besides, the photo-detectors which are arranged farther from the optical axis L1 have narrower measurable ranges.

So far, the case where the diaphragm 12b which is arranged at a conjugate position with the fundus of the emmetropic eye E has been described. As above noted, the phase difference is proportionally related to the height of the images 31a and 31b (hd') and also to the refractive power of the eye E. Therefore, even though one of the other diaphragms at a different position than the diaphragm 12b is alternatively utilized, the only change made in the mentioned relation is the position of the origin of the phase difference.

Figure 5:
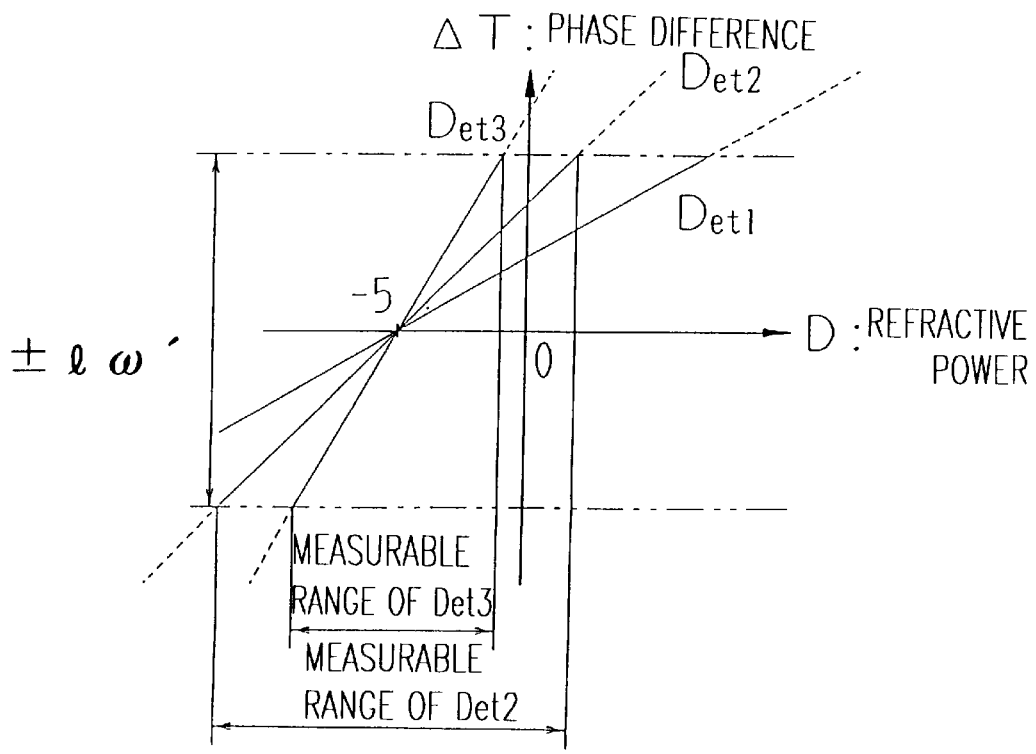
FIG. 5 is a view showing the relationship between the phase difference detected by each pair of the photo-detectors and a refractive power of the eye in the case of utilizing a diaphragm 12a which is arranged at a conjugate position with respect to a fundus of a myopic eye having a −5 [D] focal accommodation.
Figure 6:
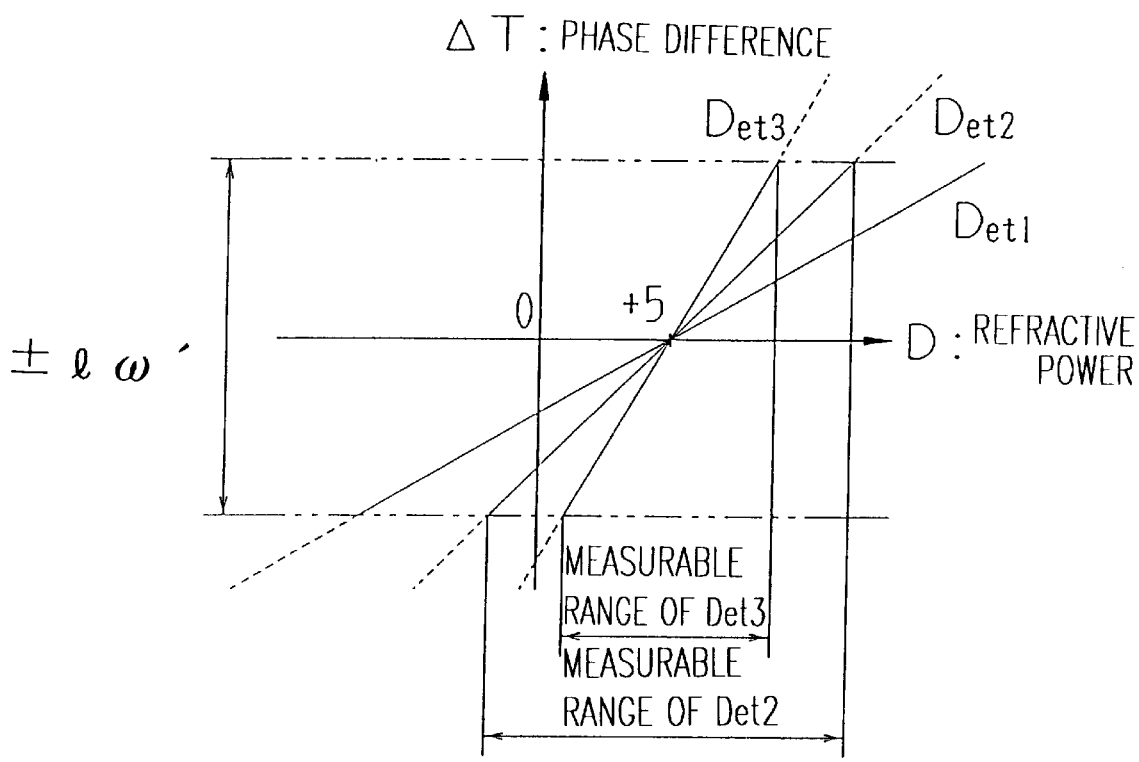
FIG. 6 is a view showing the relationship between the phase difference detected by each pair of the photo-detectors and a refractive power of the eye in the case of utilizing a diaphragm 12c which is arranged at a conjugate position with respect to a fundus of a hypermetropic eye having +5 [D] focal accommodation.

For example, in the case of utilizing the diaphragm 12a which is at a conjugate position with the fundus of the myopic eye having a −5 [D] focal accommodation, the relationship between the phase difference detected by a corresponding pair of the photo-detectors and the eye refractive power is as shown in FIG. 5. In this case, the origin where there is no phase difference is shifted to the point of an eye refractive power of −5 [D]. Accordingly, the measurable range by each pair of the photo-detectors corresponding to the range within ±lω is shifted in the same manner. Likewise, in the case of utilizing the diaphragm 12c which is at a conjugate position with the fundus of hypermetropic eye having a +5 [D] focal accommodation, the origin where there is no phase difference is shifted to the point of an eye refractive power of +5 [D], as shown in FIG. 6, and therefore the measurable range by each pair of the photo-detectors is as well shifted.

As is clear from the above, by selecting an appropriate diaphragm at an appropriate position on the optical axis (by selecting a diaphragm among 12a–12c in the case of this embodiment), a measurement range is shifted in terms of an eye refractive power, which allows the measurable range to be substantially expanded.

Next, the relationship between the photo-detectors 15g and 15h and the eye refractive power measurement will be described. In the eye refractive power measurement in accordance with this preferred embodiment, a corneal center (center of the visual axis) in a meridian direction in which the photo-detectors 15a–15f are positioned is to be obtained based on output signals from the photo-detectors 15g and 15h. Thereafter, with reference to the corneal center, an eye refractive power at a corneal part corresponding to each of the photo-detectors 15a–15f is to be obtained. In order to simplify the explanation, the pair of the photo-detectors 15a and 15b which is the closest to the optical axis L1 will be explained as an example.

Suppose that the slit light bundle is scanned at a constant speed and the waveform at the time the slit image reflected from the fundus of the eye E crosses each of the photo-detectors 15a, 15b, 15g and 15h is as is shown in FIGS. 7A–7D. This is the case that the eye E has either hypermetropia or myopia with accompanying astigmatism.

Figure 7A:
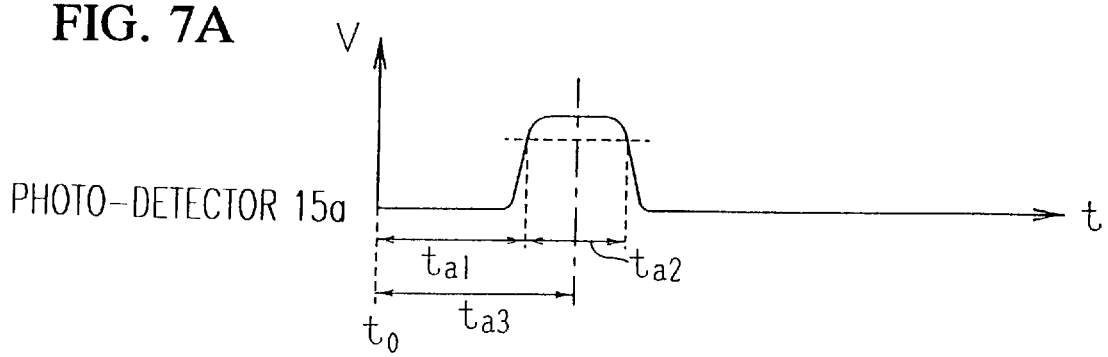
FIGS. 7A to 7D are views showing examples of waveform of output signals from respective photo-detectors 15a, 15b, 15g and 15h at a time the slit-images reflected from the fundus cross them.
Figure 7B:
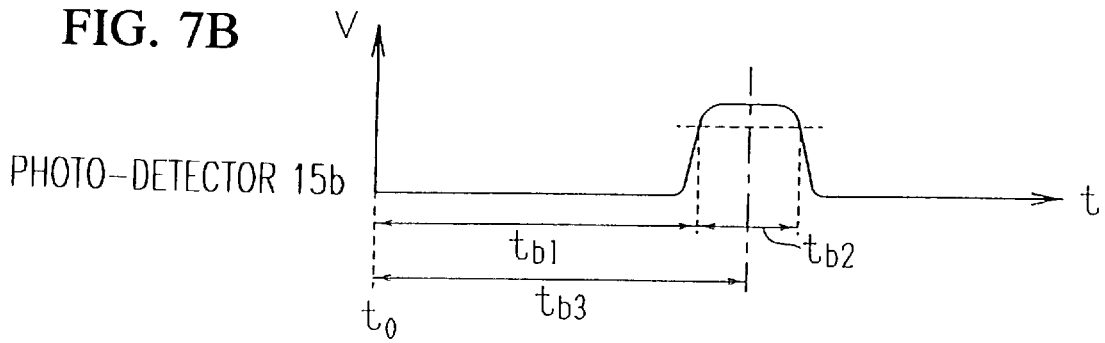
Figure 7C:
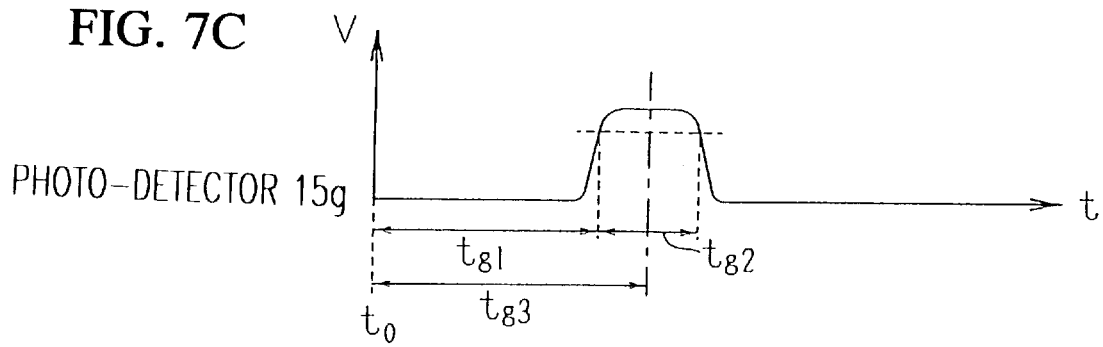
Figure 7D:
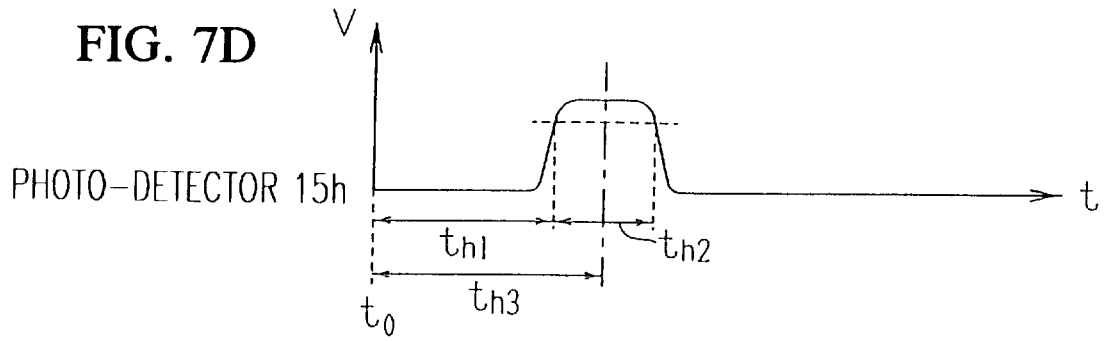

In the eye refractive power measurement based on the phase difference method, if it is assumed that eye refractive power is symmetric with respect to the corneal center (or the visual axis), the eye refractive power between the photo-detectors 15a and 15b can be obtained by matching the phase difference between the wave signal from the photo-detectors 15a shown in FIG. 7A, and the wave signal from the photo-detectors 15b shown in FIG. 7B. However, the eye refractive power is not always symmetric with respect to the corneal center. In this case, the center of the two photo-detectors 15a and 15b in the meridian direction (corresponding to the corneal center) is to be obtained based on the output signals from the photo-detectors 15g and 15h in the way described later. By determining the phase difference between the given center and signals from each of the photo-detectors 15a and 15b, the eye refractive powers at each corneal part corresponding to each photo-detector can be obtained.

First, output signals from each photo-detector 15a, 15b, 15g and 15h are conducted through a binary-converting procedure with certain threshold level and thereby form a pulse wave. Thereafter, the time difference from the time base t0 to a half of the pulse-width of pulse wave is to be detected. That is to say, with reference to FIGS. 7A–7D, ta3, tb3, tg3 and th3, which denote the time from the time base t0 to the half of the pulse-width of respective pulse wave, is given by the following expressions:

$$ta3 = ta1 + ta2/2,$$

$$tb3 = tb1 + tb2/2,$$

$$tg3 = tg1 + tg2/2, \text{ and}$$

$$th3 = th1 + th2/2.$$

Therefore, the center between the photo-detectors 15a and 15b with respect to the time base t0 is given by the following expression:

$$(tg3 + th3)/2.$$

Here, let Ta denote the time difference from the photo-detector 15a to the given center and let Tb denote the time difference from the center to the photo-detector 15b, then the following expressions are given:

$$Ta=(tg3+th3)/2-ta3$$

$$Tb=tb3-(tg3+th3)/2,$$

by calculating the time difference Ta and Tb so as to relate to the eye refractive power, it is possible to obtain the eye refractive power at the corneal part corresponding to the photo-detectors 15*a* and 15*b* with respect to the corneal center.

By applying the same procedure to the other photo-detectors 15*c*–15*f*, the respective eye refractive powers at different height with respect to the corneal center can be obtained. Thereafter, the projecting optical system 1 and the photo-receiving part 13 are made to rotate 180° about the optical axis L1 and thereby the eye refractive power in all meridian directions can be obtained.

Figure 8:
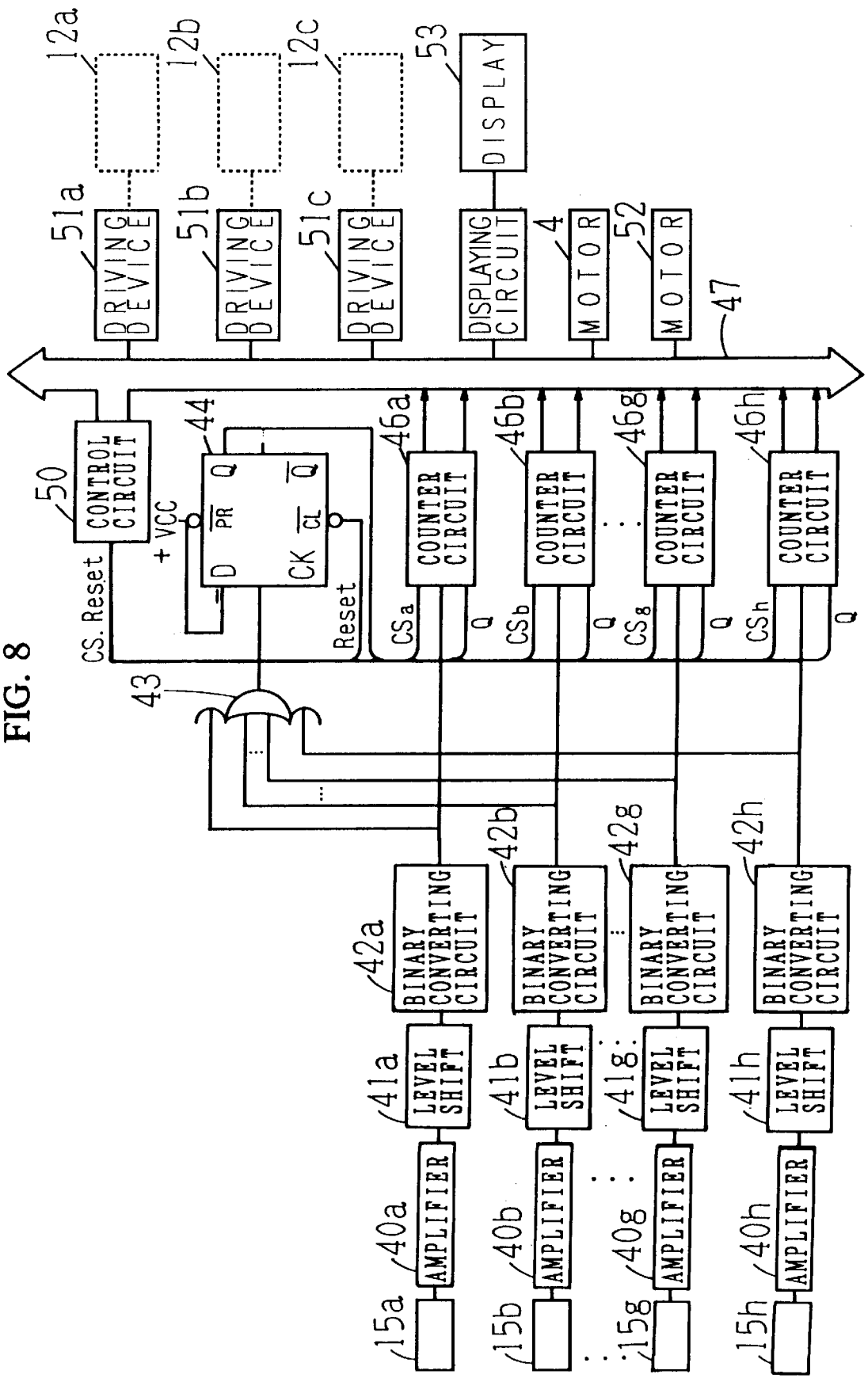
FIG. 8 is a view showing a block diagram of a signal processing system of the eye refractive power measurement apparatus according to the preferred embodiment of the present invention.

Next, the operations of the apparatus according to this embodiment will be described with reference to the FIG. 8, a block diagram of a signal processing system. Upon starting a measurement, the diaphragm 12*b* which is at a conjugate position with respect to the fundus of the emmetropic eye E is selectively adjusted to a predetermined diameter by a driving device 51*b*, whereas the other two diaphragms 12*a* and 12*c* are made to be full aperture by driving devices 51*a* and 51*c*. This operation may be carried out in response to signals generated at the time of powering on, switching over the measuring eye to the other, printing out or the like at a completion of the measurement, or the like. Under this situation, when a trigger signal is entered to a control circuit 50, a preliminary measurement is performed in a conventional way of an eye refractive power measurement based on the phase difference method and thereby obtain the eye refractive power. Based on the obtained refractive power, the projecting lens 23 included in the fixation target optical system 20 is shifted so as to place the fixation target 22 and the fundus of the eye E at conjugate positions with each other, and further appropriate amount of diopter is made to be fogged. This preliminary measurement is carried out based on the result obtained by utilizing the innermost pair of the photo-detectors 15*a* and 15*b* having the widest measurable range.

In accordance with the result of the preliminary measurement, the control circuit 50 selects one diaphragm from the diaphragms 12*a*–12*c* which secures the most appropriate measurement range in the next measurement. If the result obtained in the preliminary measurement shows that the refractive power of the eye E is −4 [D] or less, the diaphragm 12*a* is selectively adjusted. If the result shows the refractive power of the eye E is +4 [D] or more, the diaphragm 12*c* is selectively adjusted whereas the other diaphragms are made to be released. A suitable diaphragm will be selectively used in accordance with the result in the preliminary measurement (or the result obtained in a preceding measurement) if programmed to operate so in advance.

At the time of execution of a measurement, first, the projecting optical system 1 emits a slit light bundle. After having been limited by passing through the slit apertures 3*a*, the slit light bundle reaches inside the eye E so as to be projected onto the fundus of the eye E. The light bundle reflected from the fundus of the eye E passes through one of the diaphragms 12*a*–12*c* selected in the aforementioned way, then reaches the photo-receiving part 13. In the photo-receiving part 13, the reflected light bundle scans in such a manner as to cross the photo-receiving part 13 regardless of the refractive power of the eye E.

As the light bundle transmits in the photo-receiving part 13, the photo-detectors 15*a*–15*h* output photo-voltage therefrom (there is time difference between each output of the photo-voltage). The photo-voltage from each of the photo-detectors 15*a*–15*h* successively goes through corresponding amplifiers 40*a*–40*h* each of which is connected to the photo-detectors 15*a*–15*h* respectively, level shift circuits 41*a*–41*h* and reaches binary converting circuits 42*a*–42*h* whereby convert the photo-voltage into the pulse signals having binary form at the predetermined threshold level. Continually, the pulse signals are input to counter circuits 46*a*–46*h* and also to an OR circuit 43. The function of the OR circuit 43 is to set the first rising edge among the pulse signals converted by the binary converting circuits 42*a*–42*h* as the rising of the pulse for measurement, and the first rising edge is to be input to a flip-flop 44, which comes to next. The flip-flop 44 gives the pulse signals for measurement which include the time base to the respective counter circuits 46*a*–46*h*, and is reset by receiving the Reset signal output by the control circuit 50 after all pulse signals are measured.

In response to input of the pulse signals converted into the binary form in the binary converting circuits 42*a*–42*h* and also the pulse signals for measurement from the flip-flop 44, the counter circuits 46*a*–46*h* count and hold the time duration from the first rising edge of the pulse signals (the time base) to the rising edge of the pulse signals as well as the time of the pulse-width of the pulse signals respectively.

The time counted and held by each counter circuit 46*a*–46*h* is output responding to call signals (CSa–CSh) generated by the control circuit 50, and then input to the control circuit 50 through a data bus 47. Based on output from each of the counter circuits 46*a*–46*h* indicating the time duration from the time base to the rising edge of the pulse signals and the time of the pulse-width of the pulse signals in respective the photo-detectors 15*a*, 15*b*, 15*g* and 15*h*, the control circuit 50 calculates the time of the corneal center in the meridian direction for measurement in a manner mentioned above. Consequently, the time difference (the phase difference) at each one of the three pairs of the photo-detectors which are positioned in the meridian direction for measurement is obtained with respect to the given center.

Once, the time difference at each of the corneal part in one meridian direction is obtained, it is converted into the eye refractive powers with reference to the position of the diaphragm used in the measurement. There is a fixed relationship between the time difference obtained by the phase difference method and the eye refractive power. The relationship can be obtained, for example, by measuring a model eye of which refractive power is already known thereby sampling and storing the obtained data. In this way, the eye refractive power corresponding to the time difference can be easily obtained.

Next, by driving a motor 52, the components of the projecting optical system 1, from the slit illumination light source 2 to the motor 4 and also the photo-receiving part 13 are made to be rotated 180° around the optical axes L2 and L1 respectively with the predetermined intervals (for example, 1°). The eye refractive power at each rotation position is to be obtained based on the signals from the respective photo-detectors. The eye refractive power measurement is to be repeated numerous numbers of times, and the results are stored after conducting the predetermined processes (calculating the average, the medium value and the like) are carried out. In addition, the parameters S (spherical power), C (astigmatism (cylindrical) power) and A (astigmatism (cylindrical) axial angle), which are the same as the conventional art, are calculated by conducting the predetermined processes to the eye refractive power in respective meridian directions.

Once the eye refractive power at plurality of heights in each meridian direction are obtained as has been described above, the obtained data is displayed in a manner of color mapping or stereoscopic display on a display 53. For the detail of the aforementioned measurement, see U.S. patent application Ser. No. 08/942,633 or EPC Publication No. 0836830 corresponding to Japanese Patent Application No. HEI 8 (1996)-283281 by the present applicant.

The apparatus in this embodiment is equipped with three diaphragms (12a–12c), however, it is also possible to increase the number of diaphragms so as to expand the measurable range further. It is also possible to provide two diaphragms at conjugate positions with the fundus of an eye having hypermetropia and the fundus of an eye having myopia respectively so as to have the measurable ranges partially overlapped with each other. This allows to simplify the mechanism of the apparatus with assuring certain extent of measurable range.

Figure 9:
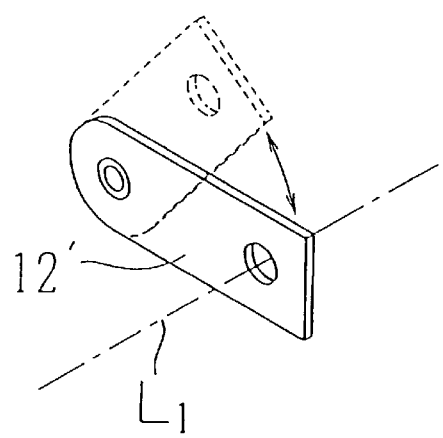
FIG. 9 is a view showing a variation in shape of the open diaphragm according to the preferred embodiment of the present invention.

Referring to a mechanism of the diaphragms (12a–12c), it is possible to apply a mechanism where a diaphragm plate 12' provided with a hole having a predetermined diameter therein as shown in FIG. 9. The diaphragm is switched by removing/inserting the diaphragm plate 12' from/on the optical path. The switching of the diaphragms may be operated manually or by switching-on and switching-off.

Figure 10:
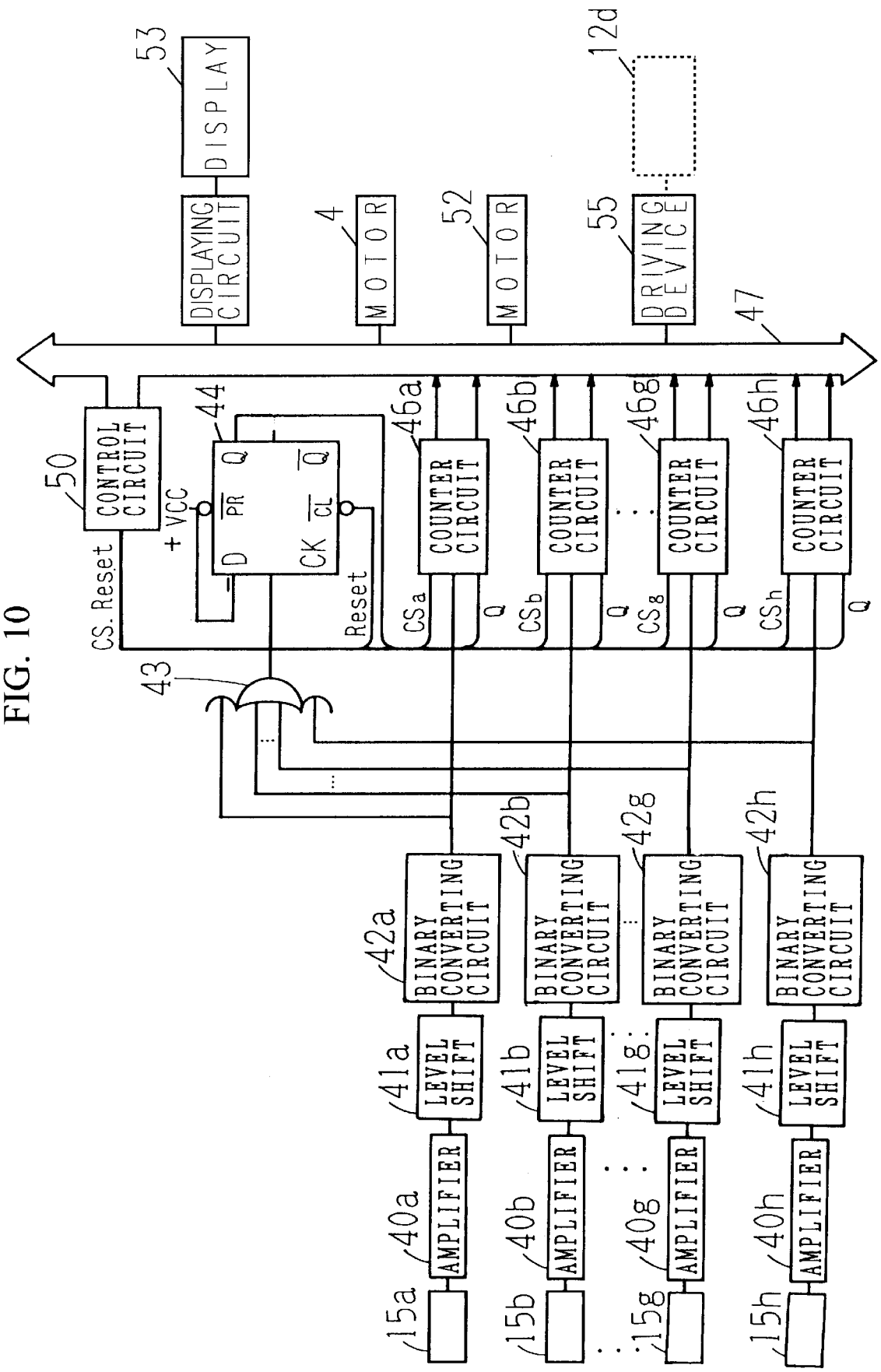
FIG. 10 is a view showing a block diagram of a signal processing system of the eye refractive power measurement apparatus according to the modified embodiment of the present invention.

In addition to the above modification, the following is also possible. Instead of plurality of diaphragms (12a–12c in the aforesaid embodiment), one diaphragm 12d having a predetermined diameter can be arranged to movable along the optical axis L1. In this case, in accordance with a result obtained in a preliminary measurement, the control circuit 50 selects a position at which the diaphragm 12d secures the most suitable measurement range and the driving device 55 moves the diaphragm 12d along the optical axis L1 to the selected position (see FIG. 10). Regarding this movement of the diaphragm 12d, it should be convenient to pre-set positions to which the diaphragm 12d should be moved in accordance with the eye refractive power which will be obtained in the preliminary measurement. For example, set one position to which the diaphragm 12d is to be moved in case of the refractive power of −4 [D] or less, set another position in case of the refractive power of +4 [D] or more, and do likewise in case of the eye refractive power other than the above. The diaphragm 12d may be moved, in accordance with the result of the preliminary measurement, manually by the examiner or by operating a switch.

The foregoing description of the preferred embodiments of the invention has been presented for purposes of illustration and description. It is not intended to be exhaustive or to limit the invention to the precise form disclosed, and modifications and variations are possible in the light of the above teachings or may be acquired from practice of the invention. The embodiments chosen and described in order to explain the principles of the invention and its practical application to enable one skilled in the art to utilize the invention in various embodiments and with various modifications as are suited to the particular use contemplated. It is intended that the scope of the invention be defined by the claims appended hereto, and their equivalents.

What is the claimed is:

1. An eye refractive power measurement apparatus for measuring a refractive power of an eye to be examined, the apparatus comprising:

a projecting optical system for scanning and projecting a slit light bundle onto a fundus of the eye to be examined;

a photo-receiving optical system comprising:

a photo-detector having at least one pair of photo-detectors arranged in one meridian direction in symmetric relation with respect to an optical axis, wherein said photo-detector is arranged at a conjugate position with a cornea of the eye so as to have a predetermined position with respect to a scanning direction of the slit light bundle, and an open diaphragm for reducing the slit light bundle, wherein said open diaphragm can be arranged at different predetermined positions;

selecting means for selecting the position of said open diaphragm based on output signals indicating the phase difference among said photo-detectors provided in said photo-receiving optical system so as to change a range in which said photo-receiving optical system can detect an eye refractive power; and eye-refractive power calculating means to calculate a refractive power of the eye based on the position of said open diaphragm and an output signal from said photo-detector receiving the slit light bundle reflected from the fundus of the eye through said open diaphragm.

2. The eye refractive power measurement apparatus according to claim 1, wherein said photo-detector provided in said photo-receiving optical system is at least one pair of photo-detectors arranged in one meridian direction in symmetric relation with respect to an optical axis and another pair of photo-detectors arranged in a different meridian direction in symmetric relation with respect to the optical axis.

3. The eye refractive power measurement apparatus according to claim 2, wherein said pair of photo-detectors arranged in the different meridian direction in symmetric relation with respect to the optical axis are to detect a corneal center based on output signals therefrom.

4. The eye refractive power measurement apparatus according to claim 1, wherein the different predetermined positions of said open diaphragm include at least two positions which are a first position which is conjugate with a fundus of a myopic eye having a predetermined eye refractive power and a second position which is conjugate with a fundus of a hypermetropic eye having a predetermined eye refractive power.

5. An eye refractive power measurement apparatus for measuring a refractive power of an eye to be examined, the apparatus comprising:

a projecting optical system for scanning and projecting a slit light bundle onto a fundus of the eye to be examined;

a photo-receiving optical system provided with a photo-detector arranged at a conjugate position with a cornea of the eye so as to have a predetermined position with respect to a scanning direction of the slit light bundle, and an open diaphragm for reducing the slit light bundle, wherein said open diaphragm can be arranged at different predetermined positions;

selecting means for selecting the position of said open diaphragm so as to change a range in which said photo-receiving optical system can detect an eye refractive power; and eye-refractive power calculating means to calculate a refractive power of the eye based on the position of said open diaphragm and an output signal from said photo-detector receiving the slit light bundle reflected from the fundus of the eye through said open diaphragm;

wherein the different predetermined positions of said open diaphragm include at least three positions which are a first position which is conjugate with a fundus of an emmetropic eye having a predetermined eye refractive power, a second position which is conjugate with a myopic eye having a predetermined eye refractive power and a third position which is conjugate with a fundus of a hypermetropic eye having a predetermined eye refractive power.

6. An eye refractive power measurement apparatus for measuring a refractive power of an eye to be examined, the apparatus comprising:

a projecting optical system for scanning and projecting a slit light bundle onto a fundus of the eye to be examined;

a photo-receiving optical system provided with a photo-detector arranged at a conjugate position with a cornea of the eye so as to have a predetermined position with respect to a scanning direction of the slit light bundle, and an open diaphragm for reducing the slit light bundle, wherein said open diaphragm can be arranged at different predetermined positions;

selecting means for selecting the position of said open diaphragm so as to change a range in which said photo-receiving optical system can detect an eye refractive power; and eye-refractive power calculating means to calculate a refractive power of the eye based on the position of said open diaphragm and an output signal from said photo-detector receiving the slit light bundle reflected from the fundus of the eye through said open diaphragm;

wherein said photo-detector provided in said photo-receiving optical system includes a plurality of pairs of photo-detectors arranged at different heights from an optical axis; and the eye refractive power measurement apparatus further comprising selecting operation control means for controlling selecting operation of said selecting means in accordance with an eye refractive power calculated by said eye refractive power calculating means from a result obtained in measurement utilizing the photo-detectors arranged closest to the optical axis.

7. The eye refractive power measurement apparatus according to claim 1, wherein said open diaphragm is a plurality of open diaphragms of which a diameter is variable arranged at different predetermined positions; and said selecting means selectively adjusts one of the open diaphragms to a predetermined diameter while making the other open diaphragms released.

8. The eye refractive power measurement apparatus according to claim 1, wherein said open diaphragm is plurality of open diaphragms of a predetermined diameter arranged at predetermined different positions on an optical axis; and said selecting means selectively inserts one of the open diaphragms into the optical axis.

9. An eye refractive power measurement apparatus for measuring a refractive power of an eye to be examined, the apparatus comprising:

a projecting optical system for scanning and projecting a slit light bundle onto a fundus of the eye to be examined;

a photo-receiving optical system provided with a photo-detector arranged at a conjugate position with a cornea of the eye so as to have a predetermined position with respect to a scanning direction of the slit light bundle, and an open diaphragm for reducing the slit light bundle, wherein said open diaphragm can be arranged at different predetermined positions;

selecting means for selecting the position of said open diaphragm so as to change a range in which said photo-receiving optical system can detect an eye refractive power; and eye-refractive power calculating means to calculate a refractive power of the eye based on the position of said open diaphragm and an output signal from said photo-detector receiving the slit light bundle reflected from the fundus of the eye through said open diaphragm;

wherein said open diaphragm, having a predetermined diameter, is arranged on an optical axis movably; and said selecting means selects a moving position of said open diaphragm and moves said open diaphragm in a direction of the optical axis.

10. The eye refractive power measurement apparatus according to claim 1, wherein said open diaphragm, having a predetermined diameter, is arranged on an optical axis movably; and said selecting means comprises moving means for moving said open diaphragm in a direction of the optical axis and movement control means for controlling said moving means based on a result obtained by said eye refractive power calculating means.

11. An eye refractive power measurement apparatus for measuring a refractive power of an eye to be examined, the eye refractive power measurement apparatus comprising:

a projecting optical system for scanning and projecting a slit light bundle onto a fundus of the eye to be examined;

a photo-receiving optical system to detect the slit light bundle reflected from the fundus of the eye by at least one pair of photo-detectors arranged in one meridian direction in symmetric relation with respect to an optical axis so as to be at an approximately conjugate position with a cornea of the eye;

eye-refractive power calculating means to calculate a refractive power of the eye based on output signals indicating the phase difference among each of said photo-detectors provided in said photo-receiving optical system;

an open diaphragm that can be arranged at different predetermined positions for reducing the slit light bundle; and selecting means for selecting the position of said open diaphragm so as to change a range in which said photo-receiving optical system can detect an eye refractive power.

12. The eye refractive power measurement apparatus according to claim 11, wherein said photo-receiving optical system further comprises a pair of photo-detectors arranged so as be symmetric with respect to the optical axis in a different meridian direction than the meridian direction that said photo-detectors are arranged.

13. The eye refractive power measurement apparatus according to claim 11, wherein the different predetermined positions of said open diaphragm include at least two positions which are a first position which is conjugate with a fundus of a myopic eye having a predetermined eye refractive power and a second position which is conjugate with a fundus of a hypermetropic eye having a predetermined eye refractive power.

14. The eye refractive power measurement apparatus according to claim 11, wherein the different predetermined positions of said open diaphragm include at least three positions which are a first position which is conjugate with a fundus of an emmetropic eye having a predetermined eye refractive power, a second position which is conjugate with a myopic eye having a predetermined eye refractive power and a third position which is conjugate with a fundus of a hypermetropic eye having a predetermined eye refractive power.

15. The eye refractive power measurement apparatus according to claim 11, wherein said photo-detectors provided in said photo-receiving optical system include a plurality of pairs of photo-detectors arranged at different heights from the optical axis; and the apparatus further comprising selecting operation control means for controlling selecting operation of said selecting means in accordance with an eye refractive power calculated by said eye refractive power calculating means from a result obtained in measurement utilizing the photo-detectors arranged closest to the optical axis.

16. The eye refractive power measurement apparatus according to claim 11, wherein said open diaphragm is a plurality of open diaphragms of which a diameter is variably arranged at different predetermined positions; and said selecting means selectively adjusts one of the open diaphragms to a predetermined diameter while making the other open diaphragms released.

17. The eye refractive power measurement apparatus according to claim 11, wherein said open diaphragm is a plurality of open diaphragms of a predetermined diameter arranged at predetermined different positions on an optical axis; and said selecting means selectively inserts one of the open diaphragms into the optical axis.

18. The eye refractive power measurement apparatus according to claim 11, wherein said open diaphragm, having a predetermined diameter, is arranged on the optical axis movably; and said selecting means selects a moving position of said open diaphragm and moves said open diaphragm in a direction of the optical axis.

19. The eye refractive power measurement apparatus according to claim 11, wherein said open diaphragm, having a predetermined diameter, is arranged on the optical axis movably; and said selecting means comprises moving means for moving said open diaphragm in a direction of the optical axis and movement control means for controlling said moving means based on a result obtained by said eye refractive power calculating means.

* * * * *

UNITED STATES PATENT AND TRADEMARK OFFICE
CERTIFICATE OF CORRECTION

PATENT NO. : 6,030,081
DATED : August 14, 2001
INVENTOR(S) : Koki Kato

It is certified that error appears in the above-identified patent and that said Letters Patent is hereby corrected as shown below:

Column 10, claim 1,
Line 4, change "a" to -- an approximately --; and
Line 5, change "so as to have" to -- and --.

Column 10, claim 5,
Line 51, "a" (first occurrence) to -- an approximately --;
Line 52, change "so as to have" to -- and --; and Column 11,
Line 4, before" myopic" insert -- fundus of a --.

Column 11, claim 6,
Line 15, change "a" (first occurrence) to -- an approximately --; and
Line 16, change "so as to have" to -- and --.

Column 11, claim 8,
Line 51, before "plurality" insert -- a --.

Column 11, claim 9,
Line 64, change "a" (first occurrence) to -- an approximately --; and
Line 65, change "so as to have" to -- and --.

Column 13, claim 14,
Line 3, before "myopic" insert -- a fundus of --.

Signed and Sealed this

Fifteenth Day of January, 2002

Attest:

JAMES E. ROGAN
*Director of the United States Patent and Trademark Office*

*Attesting Officer*